United States Patent [19]
Nash

[11] Patent Number: 5,002,549
[45] Date of Patent: Mar. 26, 1991

[54] STONE PULVERIZING APPARATUS WITH IMPROVED WORKING HEAD AND METHOD OF USE

[75] Inventor: John Nash, Downingtown, Pa.

[73] Assignee: Kensey Nash Corporation, Exton, Pa.

[21] Appl. No.: 322,754

[22] Filed: Mar. 13, 1989

[51] Int. Cl.$^5$ ............................................. A61B 17/20
[52] U.S. Cl. ..................................... 606/128; 604/22
[58] Field of Search ........ 606/127, 128, 159, 167–171, 606/180; 604/22

[56] References Cited
U.S. PATENT DOCUMENTS

| | | | |
|---|---|---|---|
| 4,679,558 | 7/1987 | Kensey et al. | 606/128 |
| 4,686,982 | 8/1987 | Nash | 128/305 |
| 4,700,705 | 10/1987 | Kensey et al. | 606/128 |
| 4,811,735 | 3/1989 | Nash et al. | 606/128 |
| 4,823,793 | 4/1989 | Angulo et al. | 606/128 |
| 4,850,957 | 7/1989 | Summers | 606/159 |
| 4,895,560 | 1/1990 | Papantonakos | 606/159 X |
| 4,907,572 | 3/1990 | Borodulin et al. | 606/128 |

*Primary Examiner*—Robert A. Hafer
*Assistant Examiner*—Kerry Owens

*Attorney, Agent, or Firm*—Caesar, Rivise, Bernstein, Cohen & Pokotilow, Ltd.

[57] ABSTRACT

A method and apparatus for destroying a stone or other hard body located within the body of a living being at a location where the stone is within a liquid. The apparatus comprises a catheter having a rotatable working head at its distal end. The working head comprises at least two radially extending blade-like members, each having plural force concentrating impacting surfaces and plural grooves. The working head is rotated at a high speed while it is in engagement with the stone. The rotation of the working head produces a flow of the liquid past the working head, with some portion of the liquid flowing through the plural grooves. The impacting surfaces impact the stone to break it into particles which are carried by the flow into repeated engagement with the impacting surfaces for further pulverization. The liquid flowing through the grooves reduces the boundary layer effect which tends to sweep smaller particles away from the impacting surfaces. Accordingly, the efficient pulverization of the particles and the destruction of the stone is effected without appreciable injury to the body of the being.

32 Claims, 2 Drawing Sheets

STONE PULVERIZING APPARATUS WITH IMPROVED WORKING HEAD AND METHOD OF USE

SPECIFICATION

This invention relates generally to medical instruments and more particularly to instruments for destroying stones or other hard bodies located within the body of a living being and methods of using said instruments.

BACKGROUND OF THE INVENTION

In U.S. patent application Ser. No. 07/079,610 filed on July 30, 1987 entitled "Stone Destroying Catheter", assigned to the same assignee as this invention, and whose disclosure is incorporated by reference herein, there is disclosed and claimed a catheter and method of use for effecting the destruction of a stone or other hard body, e.g., a body containing calcium, located within a living being.

The apparatus comprises a small diameter instrument, e.g., a catheter, having an elongated portion including a longitudinal axis and having a working head located at the distal end thereof. The elongated portion is capable of being located at a position within the body so that the working head is adjacent the stone. The working head comprises a pair of blade-like impacting members. Each blade-like member has an elongate impacting surface. The blades are arranged to move from a retracted position, wherein the impacting surface of each is located adjacent the periphery of the elongated portion of the apparatus, to an extended position, wherein the impacting surface extends substantially beyond the periphery of the elongated portion of the apparatus. The working head is arranged to be rotated at a high speed about the axis. When the working head is rotated the blades are in the extended position. Each impacting surface is arranged when rotated about the axis in the extended position to impact the stone to disintegrate or otherwise destroy the stone. The blades are oriented in a screw pitch so that when the working head is rotated they produce a powerful vortex flow in the fluid surrounding the stones which serves to draw the stones into the blades. In order to guide the stones toward (into) the rotating blades, while also protecting the surrounding body tissue from being damaged by the rotating blades, the catheter also includes shroud/guide means located adjacent the working head.

The shroud/guide means is expandable from a compact state to an expanded state. When in the compact state the shroud/guide is of an outside diameter no greater than that of the catheter to facilitate the placement of the catheter at the situs of the stone to be destroyed.

The catheter is particularly suited for destroying gallstones within the gall bladder with minimum invasion of the patient's body. As is known, gallstone are loose hard bodies located within the gall bladder, an extremely fragile, hollow structure. The catheter is arranged to be introduced while in its compact, blade-retracted state percutaneously and threaded through the patient's liver and through a small opening or puncture in the gall bladder so that the working head extends into the liquid therein. The shroud/guide means is arranged to be moved to the extended state once the working head of the catheter is in position within the liquid in the interior of the gall bladder. The catheter is then operated, that is the motor started, so that the working head commences rotation at a high rate of speed, e.g., from 5,000 to 100,000 rpm. This action causes the blades to move to the extended position.

When the shroud/guide means is in the expanded position it serves to protect the fragile wall of the gall bladder from the rotating blades. In addition, the shape of the shroud/guide means serves to direct the stones toward the rotating blades in cooperation with the vortex produced by the rotation of the blades in the liquid. Large stones which cannot fit fully into the interior of the shroud/guide means are nevertheless held within its open mouth so that the portion of the stone extending therein can be impacted by the rotating blades. This action reduces the size of the large stone, so that it can pass through the mouth fully into the blades, whereupon it is ultimately disintegrated or destroyed.

The vortex created within liquid in the gall bladder recirculates that liquid and the stones into the rotating blades so that their impacting surfaces can repeatedly impact the stones to progressively reduce the size of the stones by pulverization or fragmentation.

In order to expedite the destruction of the stones, the catheter can be utilized in conjunction with a suitable stone dissolving solvent. Such a technique may effect a more rapid disintegration of the stones as a result of the violent agitation and impaction caused by the blades, than could be otherwise achieved by the introduction of a solvent alone. Thus, a central passageway is provided down the catheter to be used to carry any suitable solvent for aiding in the destruction of the stone into the gall bladder.

After running the catheter for a predetermined period of time, e.g., ten minutes, the fluid and pulverized material produced during the stone disintegration process can be extracted or sucked out of the bladder through the catheter and fresh solvent thereafter introduced therethrough. This procedure is then repeated until all of the stones are disintegrated or destroyed.

The use of the shroud/guide means by protecting the delicate wall of the gall bladder enables the catheter to be left operating in place for a sufficiently long period of time, e.g., one hour or more, to ensure that all of the stones are destroyed or reduced to an acceptable size.

While the invention of the aforementioned patent application is suitable for its intended purposes it nevertheless leaves something to be desired from the standpoint of speed or efficiency of operation. In particular, it has been found that in gall stone lithotrite (destruction) applications, if the flow rate of the liquid in the gall bladder is increased (such as could occur by increasing the rotational speed of the working head and/or increasing the rate of flow of liquid introduced and withdrawn from the gall bladder) the faster moving liquid may carry the particles created by the stone destruction process into contact with tissue of the bladder with sufficient momentum to damage that tissue. Moreover, increasing the rate of rotation of the working head and/or the rate of flow of liquid past it results in the formation of a boundary layer of liquid flow contiguous with the blades. That boundary layer may cause the stone particles to slip by the blades and thus not be engaged by their impacting surfaces. Obviously, such action is counter productive to efficient stone destruction.

OBJECTS OF THE INVENTION

Accordingly, it is the general object of this invention to provide apparatus and methods which overcome the disadvantages of the prior art.

It is another object of this invention to provide in an instrument for mechanically destroying stones within the body of a living being an improved working head and method of use which facilitates the destruction of said stones.

It is a still further object of this invention to provide apparatus and method for mechanically destroying stones located within the body of a living being and which effects such destruction more efficiently than prior art devices and methods.

It is yet a further object of this invention to provide apparatus and method for mechanically destroying stones located within the body of a living being by pulverizing such stones into small particles quickly and without danger of injury to adjacent body tissue.

SUMMARY OF THE INVENTION

These and other objects of the instant invention are achieved by providing a method and apparatus for destroying a stone or other hard body located at a predetermined situs of liquid within the body of a living being. The apparatus has a distal end portion at which a rotary working head is located. The apparatus is introduced into the body so that the working head is in the liquid at said situs of said stone. The working head has plural, force-concentrating impacting surfaces separated by at least one relieved surface. The working head is rotated at a high speed to produce a flow of the liquid past it, with some portion of the liquid flowing through the relieved portions. The impacting surfaces impact the stone to break it into particles. The particles are repeatedly carried by the liquid flow into engagement with the impacting surfaces to effect the pulverization of the particles and the destruction of the stone without appreciable injury to the body of the being.

DESCRIPTION OF THE DRAWINGS

Other objects and many of the attendant advantages of this invention will be readily appreciated as the same becomes better understood by reference to the following detailed description when considered in connection with the accompanying drawings wherein.

DETAILED DESCRIPTION OF THE PREFERRED EMBODIMENT

Figure 1:
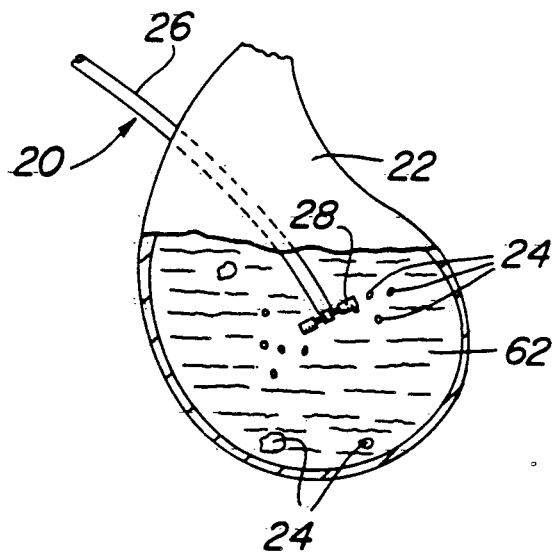
FIG. 1 is a schematic view of apparatus constructed in accordance with this invention shown located within the gall bladder of a living being to effect the destruction of stones therein.

Referring now in detail to the various figures of the drawing wherein like reference characters refer to like parts, there is shown at 20 in FIG. 1 apparatus constructed in accordance with the subject invention. That apparatus is arranged to be disposed within some body location, e.g., the gall bladder 22, in which stones 24 or other hard bodies to be destroyed are located.

In the embodiment of the apparatus 20 shown in FIG. 1 the apparatus basically comprises a catheter 26 having a rotary working head 28. The working head is arranged to draw the stones into contact with it to pulverize the stones into very small particles, so that said particles can be readily withdrawn from the patient.

The details of the working head will be described later. The details of the catheter 26 will also be described later. Suffice it to say that the catheter 26 disclosed herein is merely exemplary. Thus, other suitable types of catheters can be used with the working head 28 of this invention. In fact the working head of this invention can be used with any instrument or device which is suitable for insertion into the body at the situs of the stone to be destroyed. The use of a flexible catheter does, however, offer the advantage of facilitating the placement of the working head at the desired location within the body, e.g., it enables percutaneous or other minimally invasive insertion techniques. The positioning of the catheter 26 within the body at the desired operative situs may be effected in any conventional manner, e.g., through the use of a conventional tubular guide catheter (not shown), which is first introduced and threaded through the body to the desired position within the bladder.

Figure 2:
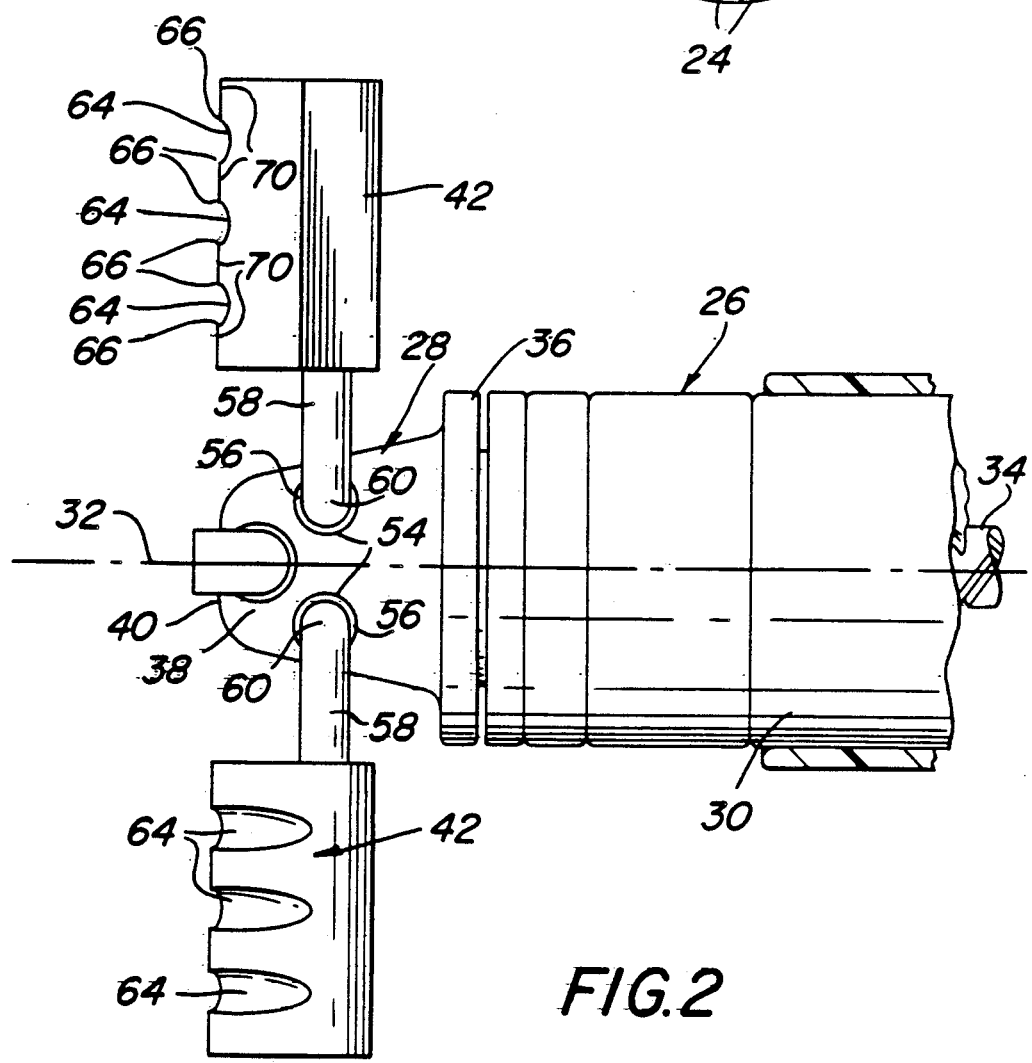
FIG. 2 is an enlarged plan view, partially in section, of the distal end portion of the apparatus shown in FIG. 1.

The catheter basically comprises an elongated outer jacket 30 of small diameter, e.g., 3-12 French (1-4 mm). The working head 28 is mounted on the distal end of the catheter 26 and is arranged to be rotated about the central longitudinal axis 32 (FIG. 2) of the catheter 26 at a high rate of speed, e.g., 10,000 to 100,000 RPM, by drive means 34 (only a portion of which is shown). The rotating working head is then brought into engagement with the stones 24 to pulverize or otherwise destroy them. The drive means can take various forms, such as an elongated drive wire or cable located within the catheter's jacket 30 and which is rotated at a high rate of speed about the longitudinal axis by a proximately located motor (not shown).

Alternatively the drive means may be constructed in accordance with the teachings in U.S. Pat. No. 4,686,982 entitled Spiral Wire Bearing for Rotating Wire Drive Catheter, and in copending U.S. patent application Ser. No. 938,698 filed on Dec. 5, 1986, entitled Catheter with Means to Prevent Wear Debris From Exiting, said patent and said application both being assigned to the same assignee as this invention, and whose disclosures are incorporated by reference herein. That drive system basically comprises an elongated drive wire or cable (not shown) supported in the center of the catheter tube, that is, along its central longitudinal axis, by means of a spiral bearing (not shown). The bearing comprises a helical or spiral coil of wire extending substantially the entire length of the catheter tube from a proximately located point outside the body to the distal end portion of the catheter. The outer diameter of helical bearing is sufficiently great so that its loops just clear the interior surface of the catheter tube to hold the bearing securely in place therein. The inside diameter of the central passage extending down the length of the helical bearing is just slightly greater than the outside diameter of the drive cable so the drive cable can rotate freely therein. In the interests of reducing the size of any wear debris created by the rotation of the drive cable within the spiral bearing, the drive cable may be swaged or drawn to increase the engaging surface area thereof, while the cross-sectional shape of the spiral bearing can be rectangular to also increase the engaging surface area as disclosed in the aforenoted copending application Ser. No. 938,698.

The high speed rotation of the working head 28 creates a vortex flow within the fluid in bladder to pull the stone into contact with the head. The rotating head includes plural impacting surfaces, to be described later, which repeatedly impact the stone at high speed to effect the stone's destruction in a similar manner as described in the aforementioned patents and applications. If necessary the catheter can be advanced along the axis 36 toward the stone during the stone destruction operation. It should be pointed out that substantial movement of the catheter's working head toward the stone is not necessary after its initial placement at the stone inasmuch as the vortex action created during the stone destruction process (which is described in detail in U.S. Pat. No. 4,679,558 and in the aforenoted U.S. patent application Ser. No. 07/079,610) tends to pull the stone into the rotating working head. In some applications, e.g., where the stone is held tightly within a lumen, it is desirable that the catheter include centering means to hold the catheter centered in the lumen to preclude injury to the lumen tissue. Such centering means is shown in my copending U.S. patent application Ser. No. 280,609, filed on Dec. 6, 1988, entitled Centered Catheter and Method of Use, which is assigned to the same assignee as this invention and whose disclosure is incorporated by reference herein. In some applications wherein the stone is held within a lumen movement of the working head toward the stone may be necessary as the stone is reduced in size, the apparatus of my aforementioned application includes means to enable the catheter to be moved centrally down the lumen during the stone destruction process.

It should be pointed out at this juncture that while the preferred embodiments of apparatus of this invention are preferably flexible to enable them to be threaded through the patient's body to the desired operative situs from what may be a remote introduction point, for some applications, e.g., where the operative site is close and can be reached by a straight or preshaped device, the apparatus need not be flexible.

Figure 4:
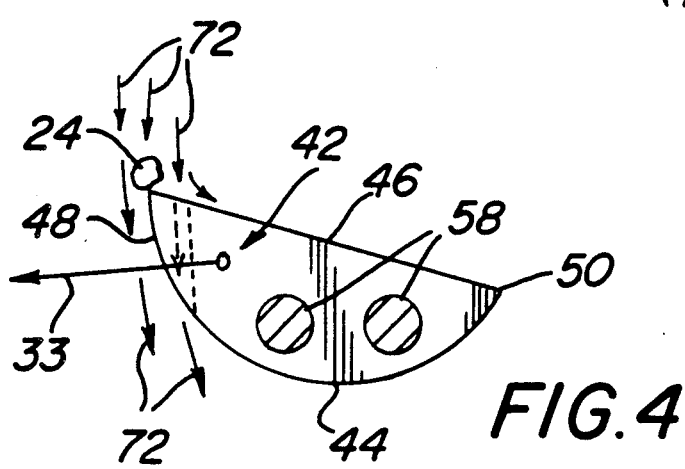
FIG. 4 is an enlarged sectional view taken along line 4—4 of FIG. 3.

The details of the working head 28 and its components will now be discussed. The working head 28 is arranged to rotate about the longitudinal central axis 32. As can be seen the working head basically comprises a base portion in the form of a circular disk 36 and from which a support hub 38 projects. The support hub basically comprise a generally thin projection centered along the axis of rotation 32 and terminating at a free end portion. A pair of blades 42 are mounted on the hub 38. Each of the blades 42 is an elongated member having a curved upper surface 44 and a planar lower surface 46 (FIG. 4). The blades, thus have the same general shape as an air foil. Each blade includes an elongated linear leading edge 48 and an elongated linear trailing edge 50. The leading edge forms the stone impacting surface of this invention, as will be described later.

Figure 3:
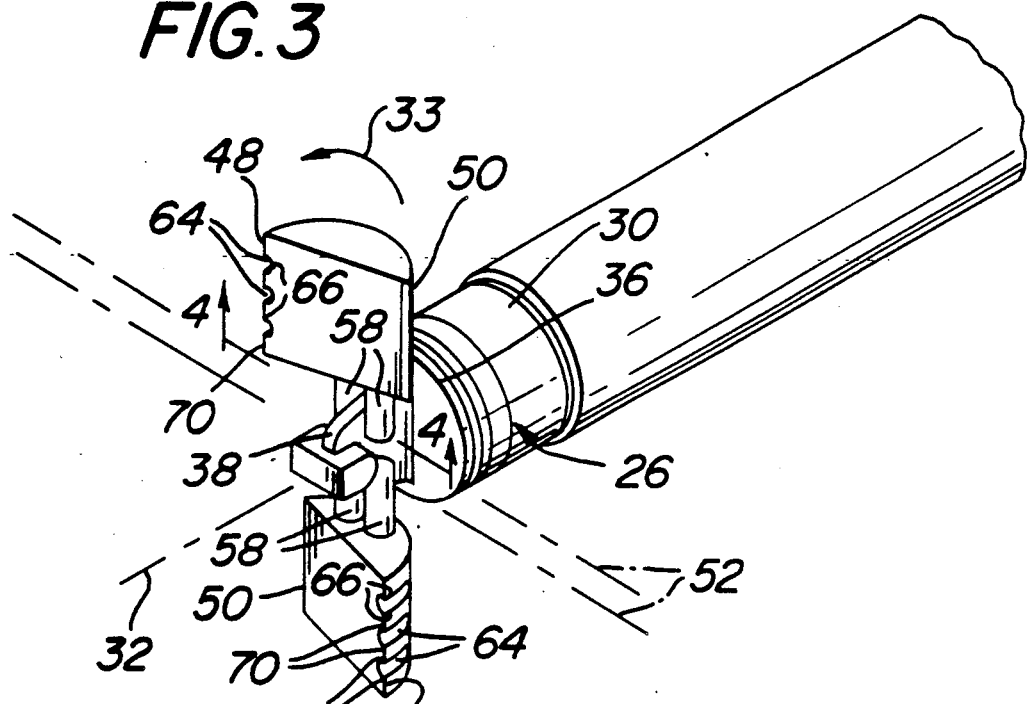
FIG. 3 is a reduced perspective view of the apparatus shown in FIG. 2.

Each blade 42 is pivotally secured to the support hub 38 to enable the blade to pivot about a respective transverse axis 52 (FIG. 3) extending perpendicularly to the axis of rotation and parallel to the sides of the hub. Thus, the hub includes a pair of holes 54 extending therethrough, with each hole centered on an axis 52. A bearing sleeve 56 may be located within each hole.

Each blade is mounted on the hub, via a respective support frame. Each frame is a generally U-shaped member having a pair of side legs 58 and an intermediate axle 60 portion. The axle portion of each frame is journalled in a respective bearing sleeve 56 and with its associated legs 58 and extending on either side of the hub 38. Each leg of each frame is fixedly secured to the blade 42 so that the blade extends outward from its support legs. The blades 42 are twisted with respect to each other to form a screw pitch. In particular the blades are twisted so that the impacting surface forming side edge 48 is the leading edge of the blade as the head rotates about axis of rotation 32. The direction of movement of the blades is shown by the arrows 33.

When the blades are in the retracted position (not shown) they lie generally along respective axes extending generally parallel to the axis of rotation 32 or at a slight outward angle with respect thereto. As the working head rotates the centrifugal force on the blades causes the blades to pivot outward about the respective transverse axes 52 to an extended position, shown in FIGS. 1-3, whereupon the blades extend up to a maximum angle, e.g., 90°, with respect to the axis of rotation. With the blades in this orientation and rotating about axis 32 their screw pitch produces a powerful vortex which is directed generally inward toward the center of the working head. This vortex recirculates the liquid 62 and stones 24 within the gall bladder into the rotating blades 42 to effect the progressive size reduction (destruction) thereof.

As will be appreciated by those skilled in the art, if the blades were of a fixed size so that they did not extend substantially beyond the outside diameter of the catheter they would tend to bore a hole in large stones rather than to fragment them. By having the blades pivot outward to a position substantially beyond the outer diameter of the catheter itself one can create a very powerful vortex (the power in a vortex is proportional to the blade diameter to the fifth power). It is also contemplated that the blades may be weighed at their free ends or otherwise constructed to include heavy tips providing a large mass at the radially outward position, thereby providing higher kinetic energy to aid in the stone destruction process.

In accordance with the teachings of this invention each of the blades includes a plurality of relieved portions or grooves 64 in the leading edge 48. The grooves are of a predetermined width, e.g., 0.5 mm, and are equidistantly spaced along the blades, e.g., at 0.5 mm spacing. The leading edge 48 of each blade is sharp, hence a point-like impacting surface 66 is produced at the junction of the leading edge with each side of a groove 64. These plural point impacting surfaces form what can be termed a line contact fracturing device which is quite efficient in breaking up or pulverizing the stone and its resulting particles without increasing the liquid flow rate (which action could result in tissue damage, e.g., hemorrhage, due to the "sand blasting" effects of the particles impacting the tissue). In this regard, as will be appreciated by those skilled in the art each point contact impacting surface 66 concentrates the impacting force on the stone particle 24 engaged to expedite its breakage into smaller particles. Moreover the short leading edge portions 70 between the grooves 64 also form impacting surfaces. Being of short length those impacting surfaces also concentrate an impacting force onto the particles 24 engaged thereby.

Figure 5:
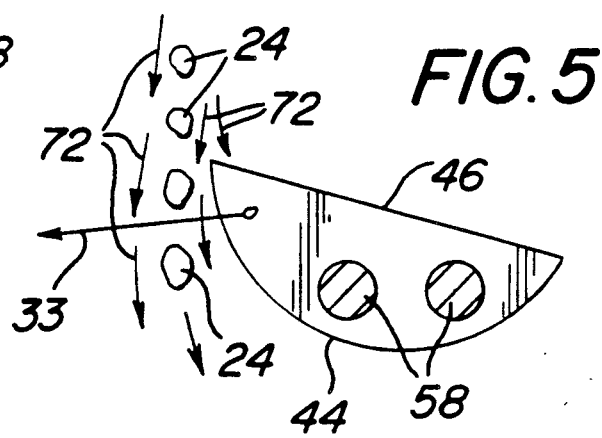
FIG. 5 is a view similar to that of FIG. 4 but showing a blade of a working head like that disclosed in the aforementioned U.S. application Ser. No. 07/079,610.

As will also be appreciated by those skilled in the art, the grooves 44 provide relief for the liquid (denoted by the arrows 72) flowing by the blades as shown in FIG. 4. This "scouring" action reduces the boundary layer effect which is created at blades which do not have grooves. Such a boundary layer tends to sweep smaller particles past (away) from the ungrooved blades without impact as shown in FIG. 5. The combined effect of the higher stress from the point impact portions 66 and short line impact portions 70 and the better access to those portions by the stone particles 24 due to aforementioned "scouring" action on the boundary layer reduces stone destruction operating time and particle size.

It has been found that in some applications it may be desirable to periodically rotate the working head in the opposite direction as the normal direction in order to clear the working head of any entrapped stones or fragments. Hence the drive system is arranged to rotate the working head in either direction upon command.

The working head may also include at least one aperture (not shown) to the exterior thereof and in fluid communication with the interior of the catheter. This aperture, can also provide a means for introducing a solvent or other liquid into the body at the situs of the stone to be destroyed, while also serving as a passageway through which the stone fragments can be extracted by suction through the catheter.

It should also be noted that while the catheter and its method of use as described heretofore has focused on the destruction of gall stones, it should be clear that the subject catheter can be utilized to destroy any type of stone located within the body of a living being, and whether the stone is free floating (that is, located loosely within a body organ or tissue), or closely confined (that is, constrained or held within some body portion, e.g., a duct, etc.). In the former case the use of the vortex is of considerable importance whereas in the latter case it is of less importance.

In accordance with the preferred embodiment of the invention the working head, and in particular its blades, is formed of a tough and impact resistant material, such as a suitable metal, alloy, plastic, etc.

Without further elaboration, the foregoing will so fully illustrate my invention that others may, by applying current or future knowledge, readily adopt the same for use under various conditions of service.

I claim:

1. A method for destroying a stone or other hard body located at a predetermined situs of liquid within the body of a living being, said method comprising introducing a member into said body, said member having a distal end portion at which a rotary working head is located, said working head comprising at least two radially extending elongated members, each having at least one force-concentrating impacting surface and at least one relieved surface, rotating said working head at a high speed, said impacting surface impacting said stone and applying a concentrated impact force thereto to break said stone into smaller particles, said working head being configured so that the rotation of said working head creates a vortex-like flow of said liquid past said working head, whereupon said particles are repeatedly carried by said flow into engagement with said impacting surface, said relieved surface being configured so that upon said rotation of said working head some portion of said liquid is caused to pass through said relieved surface to reduce the boundary layer effect which tends to sweep smaller particles away from said impacting surface, to thereby effect the efficient pulverization of said particles and the destruction of said stone.

2. The method of claim 1 wherein the momentum imparted to said particles is kept sufficiently low so that no appreciable injury to the body of said being occurs during said stone destruction process.

3. The method of claim 1 wherein said predetermined situs comprises the gall bladder, and wherein said stone comprises a gall stone.

4. The method of claim 1 wherein said apparatus comprises a flexible catheter.

5. The method of claim 2 wherein said apparatus comprises a flexible catheter.

6. The method of claim 1 wherein said impacting surfaces comprises a point surface.

7. The method of claim 1 wherein impacting surface comprises a short line surface.

8. The method of claim 1 wherein said impacting surface comprises at least one point surface and one short line surface.

9. The method of claim 1 wherein liquid is introduced into said body at the situs of said stone to aid in the stone destruction process.

10. The method of claim 9 where said liquid and said particles are removed from said body.

11. Apparatus for destroying a stone or other hard body located at a predetermined situs within the body of a living being, said stone being located within a liquid at said situs, said apparatus comprising a elongated member having a distal end portion at which a rotary working head is located, said working head comprising at least two radially extending elongated members, each having at least one force-concentrating impacting surface and at least one relived surface, means for rotating said working head at a high speed, said impacting surface impacting said stone and applying a concentrated impact force thereto to break said stone into smaller particles, said working head being configured so that the rotation of said working head creates a vortex-like flow of said liquid past said working head, whereupon said particles are repeatedly carried by said liquid into engagement with said impacting surface, said relieved surface being configured so that upon said rotation of said working head some portion of said liquid is caused to pass through said relieved surface to reduce the boundary layer effect which tends to sweep smaller particles away from said impacting surface, to thereby effect the efficient pulverization of said particles and the destruction of said stone.

12. The apparatus of claim 11 wherein said apparatus comprises a flexible catheter.

13. The apparatus of claim 11 wherein said impacting surface comprises a point surface.

14. The apparatus of claim 11 wherein said impacting surface comprises a short line surface.

15. The apparatus of claim 11 wherein said impacting surface comprises at least one point surface and one short line surface.

16. The apparatus of claim 15 wherein each of said elongated members comprises plural point surfaces and short line surfaces.

17. The apparatus of claim 16 wherein said point surfaces are separated from each other by approximately 0.5 mm.

18. The apparatus of claim 17 wherein said line surfaces are approximately 0.5 mm long.

19. The apparatus of claim 11 wherein each of said elongated members has a leading edge, and wherein said relieved surface comprises a groove in said leading edge.

20. The apparatus of claim 19 wherein at least one portion of said leading edge contiguous with said groove is sharp to form at least one point shaped impact surface contiguous with said groove.

21. The apparatus of claim 20 wherein said one leading edge portion forms at least one line shaped impact surface located closely adjacent said groove.

22. The apparatus of claim 20 wherein each of said elongated members comprises plural point shaped impact surfaces separated from each other by approximately 0.5 mm.

23. The apparatus of claim 21 wherein each of said elongated members comprises plural line shaped impact surfaces, each of said line shaped impact surfaces being approximately 0.5 mm long.

24. The apparatus of claim 22 wherein each of said elongated members comprises plural line impact surfaces, each of said line impact surfaces being approximately 0.5 mm long.

25. The apparatus of claim 11 wherein said apparatus comprises a flexible catheter.

26. The apparatus of claim 11 wherein each of said elongated members is a blade-like member, with said members being oriented with respect to each other to form a screw pitch.

27. The apparatus of claim 26 wherein each of said blade-like members has a leading edge, and wherein said relieved surface comprises a groove in said leading edge.

28. The apparatus of claim 27 wherein at least one portion of said leading edge contiguous with said groove is sharp to form at least one point shaped impact surface contiguous with said groove.

29. The apparatus of claim 28 wherein said one leading edge portion forms at least one line shaped impact surface located closely adjacent said groove.

30. The apparatus of claim 29 wherein each of said blade-like members comprises plural point shaped impact surfaces separated from each other by approximately 0.5 mm.

31. The apparatus of claim 30 wherein each of said blade-like members comprises plural line shaped impact surfaces, each of said line shaped impact surfaces being approximately 0.5 mm long.

32. The apparatus of claim 31 wherein said apparatus comprises a catheter.

* * * * *